United States Patent

Karami et al.

Patent Number: 5,244,457
Date of Patent: Sep. 14, 1993

[54] VENTED WOUND DRESSING

[75] Inventors: Hamzeh Karami, Mansfield; Ronald F. Vitaris, Worcester, both of Mass.

[73] Assignee: The Kendall Company, Mansfield, Mass.

[21] Appl. No.: 856,413

[22] Filed: Mar. 23, 1992

[51] Int. Cl.⁵ .................. A61F 13/00; A61F 15/00; A61L 15/00

[52] U.S. Cl. .................. 602/55; 602/43; 602/47; 602/54; 602/58; 602/59; 604/304; 604/307

[58] Field of Search .............. 604/304, 307, 358, 378, 604/383, 385.1; 602/47, 48, 41-46, 52, 54-55, 57-59, 78-79; 128/888

[56] References Cited

U.S. PATENT DOCUMENTS

| | | | |
|---|---|---|---|
| 2,399,545 | 4/1946 | Davis | 602/55 |
| 3,457,919 | 7/1969 | Harbard | 602/55 |
| 3,811,438 | 5/1974 | Economou | 602/55 |
| 3,888,247 | 6/1975 | Stenvall | 602/59 |
| 4,499,896 | 2/1985 | Heinecke | 602/57 |
| 5,010,883 | 4/1991 | Rawlings et al. | 602/52 |
| 5,056,510 | 10/1991 | Gilman | 602/59 |
| 5,086,763 | 2/1992 | Hathman | 602/79 |

Primary Examiner—Randall L. Green
Assistant Examiner—A. Zuttarelli
Attorney, Agent, or Firm—Alvin Isaacs

[57] ABSTRACT

Disclosed is a vented dressing comprising a thin conformable vapor-permeable, liquid-impermeable sheet material having a generally centrally disposed wound-covering portion for placement directly over the wound and a peripheral portion defining the central portion and which is intended to be secured to the whole skin surrounding the wound, the sheet material having a coating of a pressure-sensitive adhesive extending substantially entirely over one surface thereof for adhering the dressing to the body, the adhesive coating being applied so as to provide repeating areas containing no adhesive, areas of the wound-covering portion of the sheet material where there is no adhesive having slits extending through the thickness thereof to permit venting of wound fluids therethrough, the areas of no adhesive in peripheral portion being free of any slits whereby passage of wound fluids therethrough is precluded, the peripheral areas of the sheet material having no adhesive however permitting vapor transmission therethrough whereby to inhibit maceration of the skin beneath the peripheral areas.

30 Claims, 3 Drawing Sheets

VENTED WOUND DRESSING

BACKGROUND OF THE INVENTION

It is most desirable in wound treatment to provide an adhesive dressing which will maintain the desired moist environment promoting healing while preventing scab formation; and also permitting removal of wound fluid which can build up to a pressure bubble beneath the dressing, thereby undermining the adhesive seal to the skin and thus increasing the possibility of the wound being contacted by ambient contaminants, including, of course, microorganisms which can cause infection.

Seemingly, these two objectives are often at cross-purposes so that one of the two desired objectives is accomplished to the detriment of the other.

Yet, dressings fulfilling both objectives are heretofore disclosed in the art.

By way of illustration, reference may be made to U.S. Pat. No. 4,541,426 issued to Webster and the vented dressings described and claimed in U.S. Pat. No. 5,056,510 and copending application, Ser. No. 337,591 filed Apr. 13, 1989 and now U.S. Pat. No. 5,106,362, both in the name of Thomas H. Gilman and assigned to The Kendall Company, assignee of the instant invention.

A particularly efficacious wound dressing permitting removal of wound fluids while maintaining a moist environment is the vented dressing disclosed in the copending application of Hamzeh Karami and Thomas H. Gilman, Ser. No. 738,983 filed Jul. 29, 1991, and also assigned to the common assignee.

As is described and claimed therein, the vented wound dressing comprises a thin conformable sheet material, at least a portion of which is adapted for placement over a wound having a pressure-sensitive adhesive layer on one surface thereof, the adhesive layer being applied to provide repeating spaced areas free of adhesive. Preferably the non-adhesive areas are arranged in a geometric pattern. In any case, while the non-adhesive areas are shown for purposes of illustration as being generally circular, the configuration is not critical and they may be of any desired shape, e.g. oval, rectangular, arcuate, etc.

At least a portion of the repeating areas of no adhesive have slits extending through the thickness thereof to permit transfer of wound fluids through the sheet material unimpeded by the presence of adhesive material which can clog the slits and thereby inhibit fluid transfer therethrough.

As is further described and claimed therein, the aforementioned vented dressing, which will be termed hereinafter as the "primary dressing", meaning the dressing attached to the skin and covering the wound, will additionally contain thereover what is hereinafter termed a "secondary dressing" including an aborbent pad or the like providing a reservoir for receiving and retaining wound fluids diffusing through the slits in the primary dressing. Most preferably, a cover sheet providing a bacterial barrier is situated over the reservoir.

While providing an elegant wound dressing of simplified construction permitting removal of wound fluids while at the same time maintaining a moist environment conducive to wound healing, the dressing does not address the problem of skin maceration which can occur in the healthy, intact skin surrounding the wound covered by the adhesive of this dressing.

Stated simply, the task of this invention is to devise a means in the vented dressings of the aforementioned Ser. No. 738,983 for preventing skin maceration. In this context, the present invention may properly be said to be directed to an improvement in the vented dressings of this copending application.

BRIEF DESCRIPTION OF THE INVENTION

In accordance with the present invention, this task is solved in an elegant manner by also providing repeating areas of no adhesive in the peripheral portion intended to be applied to cover healthy intact skin surrounding the wound in order to secure the dressing in a bacteria-free fluid-tight manner, the sheet material in these adhesive-free areas being free of slits so as to provide a barrier to fluid transfer, the vapor-permeable sheet material however permitting vapor transmission therethrough whereby to inhibit maceration of the underlying skin.

DETAILED DESCRIPTION OF THE INVENTION

As was heretofore mentioned, the present invention is directed to a vented dressing of the type disclosed in the aforementioned copending application, Ser. No. 738,983 wherein the primary dressing applied to cover the wound comprises a thin, conformable, liquid-impermeable, vapor-permeable sheet material having an adhesive coating on one surface thereof for adhering the dressing to the skin, the adhesive coating in this portion of the dressing for placement over the wound being applied so as to provide repeating areas containing no adhesive, areas of the sheet material where there is no adhesive having slits extending through the thickness thereof to permit venting of wound fluids therethrough, the essence of the present invention being also providing repeating areas of no adhesive in peripheral portions of the sheet material surrounding the wound-covering portion for adherence to intact skin surrounding the wound, the areas of no adhesive in the peripheral portions of the sheet material containing no slits whereby they are a barrier to diffusion of wound fluids while permitting vapor transmission so as to inhibit maceration of the skin underlying these peripheral portions.

The nature and objects of the invention may best be understood by references to the accompanying drawings taken in conjunction with the following detailed description.

Figure 1:
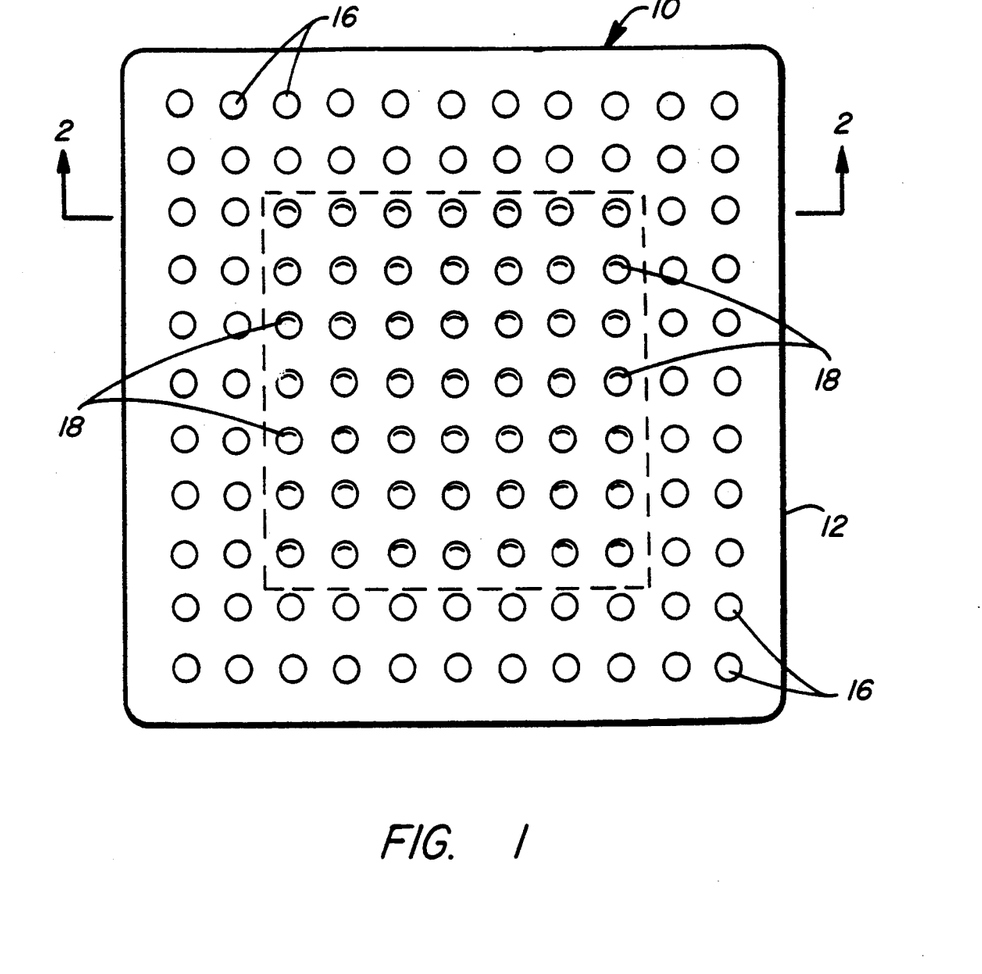
FIG. 1 is a bottom view of the primary dressing for placement on the wound.
Figure 2:
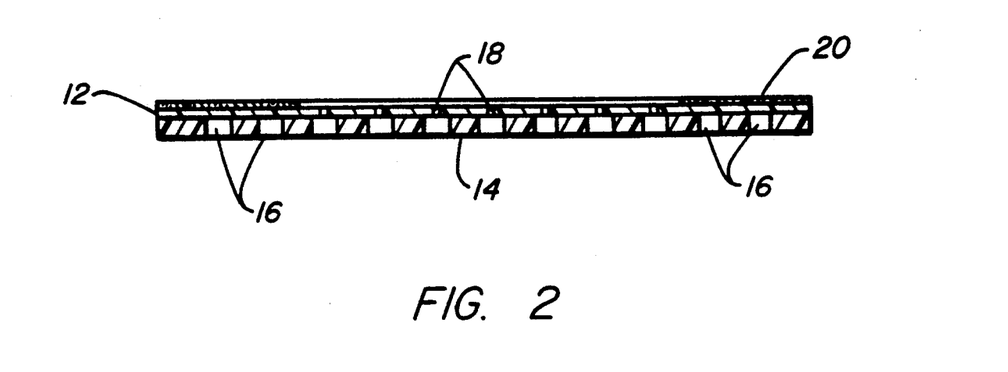
FIG. 2 is a sectional view of the primary dressing taken along lines 2—2 of FIG. 1.

With reference to FIGS. 1 and 2, the primary dressing 10 of this invention for placement on the wound will comprise a thin conformable sheet material 12 having a per se known pressure-sensitive adhesive layer 14 on the underlying surface thereof, the adhesive layer being applied to provide repeating spaced areas 16 free of adhesive. As is stated in the aforementioned Ser. No. 738,983 and seen, for example, in FIG. 1, the adhesive-free areas are isolated by the adhesive areas forming a dam or barrier inhibiting lateral diffusion of the exudate. Preferably the non-adhesive areas are arranged in a geometric pattern, e.g. in aligned rows, as shown in the drawing, or in staggered rows. In any case, while the non-adhesive areas 16 are shown for purposes of illustration as being generally circular, the configuration is not critical and they may be of any desired shape, e.g. oval, rectangular, arcuate, etc.

In the illustrative configuration shown in FIG. 1, the primary dressing is generally square and has a total of eleven adhesiveless areas in each row, both horizontal and vertical. The outer two horizontal and vertical rows are positioned in peripheral portions of the dressing intended for adherence to intact skin surrounding the wound areas. These peripheral portions define a generally centrally disposed portion consisting of non-adhesive areas 3-7 in each direction, which centrally disposed portion is intended to be placed directly over the wound.

Slits 18 are shown to be provided within each of the non-adhesive areas in the wound-covering portion. However, it is within the scope of this invention to provide slits in less than all of these non-adhesive areas, if found desirable to do so.

While the slits 18 are shown in FIG. 1 to be somewhat arcuate in shape, they may have other forms. For example, they may be "x-shaped", or, as shown in the aforementioned U.S. Pat. No. 4,541,426 of Webster, they may be linear or in the form of triangular flaps provided by slitting two sides of the triangle so that the flaps remain attached by the third side. In any case, as shown in the drawings, however, the slits will have dimensions smaller than the non-adhesive areas where they are positioned so that each slit can be said to occupy only a portion of each non-adhesive area in which it is contained.

As previously mentioned, the present invention is directed to the problem of maceration which can occur to the healthy skin surrounding the wound due to occlusion of water from transepidermal water loss under the overlying adhesive layer.

This task is solved by providing in this portion of the primary dressing repeating areas of non-adhesive which can be the same or different from those in the wound-covering portion of the dressing having slits to permit diffusion of exudate. However, since the passage of fluid from or into the dressing in these peripheral portions is not desirable, the peripheral non-adhesive areas will not have slits so they will be characterized as being fluid-impermeable but vapor-transmissive.

In the illustrative drawing two rows of these non-adhesive areas 16 are shown to be slit-free.

While the primary dressing shown in FIGS. 1 and 2 finds utility by itself, it is particularly intended to be used in combination with a secondary dressing providing a reservoir for receiving wound fluids diffusing through the slits, which secondary dressing is releasably secured to the primary dressing so as to be readily replaceable on an as needed basis without disturbing the primary dressing covering the wound.

The secondary dressings envisioned in the practice of this invention will include an absorbent pad or other per se known equivalent fabric and an overlying cover sheet providing a bacterial barrier. The cover sheet will have a layer of pressure-sensitive adhesive around its periphery to releasably secure the secondary dressing to the primary dressing. Most preferably, at least a portion of the cover providing a bacterial barrier is also air-permeable to permit egress of air from the interstices or voids in the fabric reservoir to the ambient atmosphere. As will be appreciated, removal or displacement of entrained air within the fabric reservoir is necessary to free these interstices to act as a sponge for retention of wound fluids diffusing thereto, thereby appreciably increasing the capacity of the reservoir for receiving and retaining wound fluids.

As heretofore mentioned, the secondary dressing is most preferably readily separated from the primary dressing in order to observe the wound and/or to replace it with a fresh new one.

Figure 4:
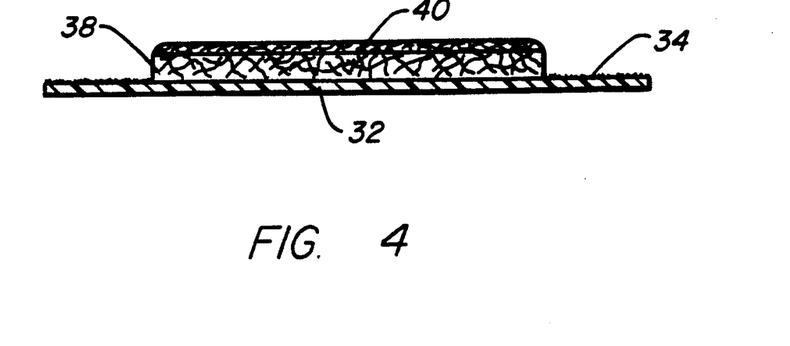
FIG. 4 is a sectional view taken along lines 4—4 of FIG. 3.

To facilitate this easy removal, in the preferred embodiment envisioned by this invention at least the periphery of the non-adhesive-bearing surface of the sheet material 12 to be contacted by the adhesive coating by the adhesive coating on the secondary dressing will have a release coating 20 of known description, as seen in FIGS. 2 and 4. The concept of providing the release coating 20 to facilitate removal of the secondary dressing from the vented primary dressing is described and claimed in our concurrently filed copending application, Ser. No. 856,415.

Figure 3:
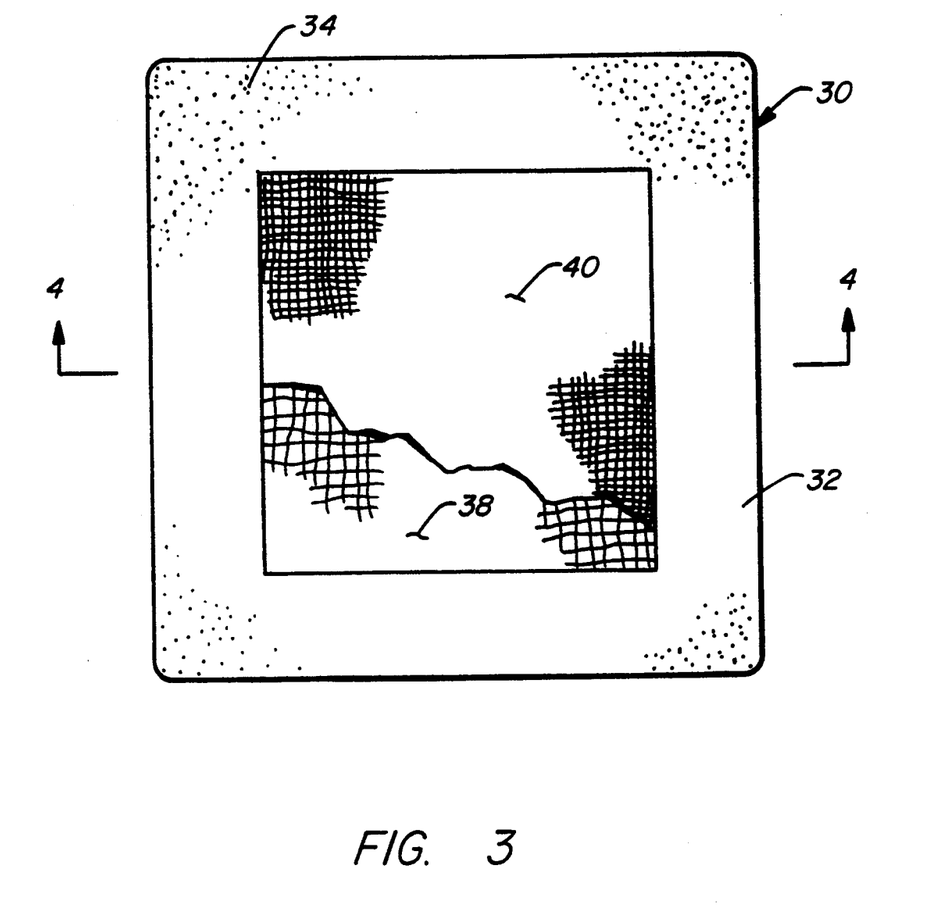
FIG. 3 is a perspective view of the preferred secondary dressing partially broken away to reveal the arrangement of elements.

While the reservoir in the secondary dressing may comprise any of the fabric materials heretofore employed to retain exudate, e.g. cotton, gauze sponges, absorbent pads such as those customarily used for abdominal surgery, and the like, in the most preferred enbodiment of this invention, it will consist of two separate but contiguous elements, namely a lower high density woven or non-woven fabric having optimum spreading or wicking characteristics, and an upper low density fabric having optimum absorption capacity. The concept of providing such a combination of high and low density fabrics in the secondary dressing is illustrated in FIGS. 3 and 4 and is described and claimed in the concurrently filed copending application, Ser. No. 856,414.

As best seen in FIG. 3, in the best mode contemplated for the practice of the instant invention, the secondary dressing 30 will comprise a high density fabric 40 and an overlying low density fabric 38 which together form a reservoir for receiving and retaining wound exudate. Preferably, the high density fabric will have a density of on the order of 0.1 to 0.2 gms/(cm)$^3$; while the low density fabric will have a density less than 0.1, e.g. on the order of 0.05 gms/(cm)$^3$. In a typical embodiment, the combination of fabrics 38 and 40 will provide a weight per surface area of on the order of 7 ounces/square yard, the ratio of low:high density by thickness being on the order of about 3:1 to about 5:1. The fabrics may be woven or non-woven materials, non-woven being preferred, and illustrative fibers include rayon, rayon/polyester or polyester/cotton blends, cotton, cellulosic materials, etc.

With reference again to FIG. 3, the secondary dressing 30 will have a bacteria-impermeable, air-permeable cover sheet 32. As heretofore alluded to, in addition to the cover sheet providing a barrier to ingress of bacteria which could then pass through the slits 18 in sheet material 12 of the primary dressing and then to the underlying wound, the cover sheet 32 should additionally be air-permeable to permit egress of air from the interstices or voids in the fabric reservoir to the ambient atmosphere. Suitable materials for this purpose include polyurethane, a polyolefin such as polyethylene or polypropylene, "Saran" (trademark of Dow Chemical). a polyester such as polyethylene terephthalate, etc.

The cover sheet 32 should also have a layer of pressure-sensitive adhesive 34 in its peripheral portions surrounding the fabric reservoir in order to seal the cover sheet in liquid—and bacteria—tight relationship around their common periphery so that exudate cannot escape through the edges of the dressing, nor can any external contaminants, including bacteria, enter into the dressing and then pass through the slits 18 to the underlying wound. To provide such a barrier, the adhesive layer 34 may, for example, be on the order of 10 mils thick. If desired, adhesive layer 34 may also be applied so as to provide recurring areas of no adhesive to increase vapor transmission.

While the cover sheet 32 may be a single sheet material, as shown in FIGS. 3 and 4, it is within the scope of this invention to provide a cover sheet of the type shown in U.S. Pat. Nos. 5,060,642 and 5,056,510 as well as the aforementioned copending application, Ser. No. 738,983, wherein the cover sheet is provided with one or more windows or openings each of which is covered by an air-permeable bacterial barrier sheet material, e.g. one of the per se known bacterial barrier air filters such as NUCLEOPORE, MILLIPORE, GELLMAN, etc.

Notwithstanding the bacterial barrier aspects of the cover sheet and the adhesive securing the cover sheet to the rear surface of the primary dressing, where found desirable to assure the proper bacteria-free environment, an antimicrobial agent such as chlorhexidine may be included in the absorbent pad reservoir. However, the use of such a reagent is not considered necessary in the practice of this invention.

As was previously mentioned, secondary dressings of this description are described and claimed in copending application Ser. No. 856,414.

Figure 5:
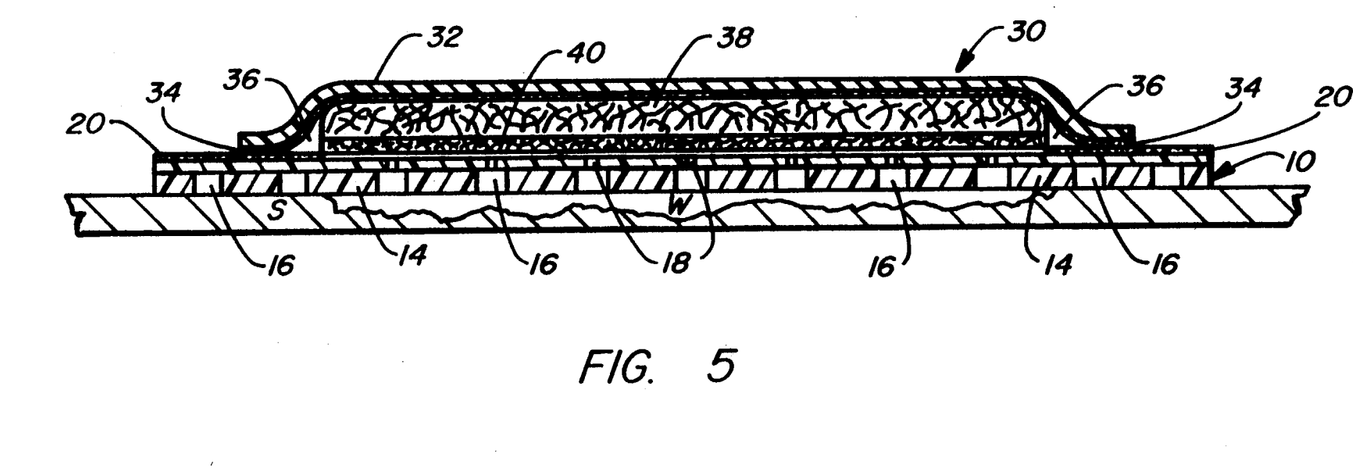
FIG. 5 is a sectional view showing the arrangement of the primary and secondary dressings in accordance with this invention.

With reference now to FIG. 5, the relationship of the primary and secondary dressings in accordance with the invention may best be understood.

The primary dressing 10 is applied to cover the wound W with the peripheral portions free from slits 16 overlying the healthy intact skin S.

The secondary dressing 30 is then placed over the primary dressing, most preferably with the absorbent pads 38, 40 squarely aligned with the edges of the outermost rows of non-adhesive areas having slits. This is readily observable by the clinician, thereby facilitating proper placement of the secondary dressing. When so positioned, the surface of cover sheet 32 bearing adhesive 34 will be superposed over and in direct contact with the release coating 20 on the outer surface of sheet 12 of the primary dressing.

When so positioned, an elegant dressing is provided whereby wound exudate is permitted to diffuse through the slits in the primary dressing to the overlying secondary dressing where the exudate is wicked into the fabric reservoir and there absorbed. The slits permit the dressing to maintain a moist environment promoting wound healing while at the same time preventing reflux or "back diffusion" of exudate from the secondary dressing back into the wound. The adhesive 14 securing the primary dressing, outer cover 32, and the adhesive 34 securing the respective dressings together provide an environment for wound healing effectively precluding bacteria and any other external contaminants.

When it is desired to remove the secondary dressing either to observe the healing process or to replace it with a new one when the capacity of the reservoir to retain wound fluid is about to be reached, the release coating 20 renders separation easy without pulling on and/or displacing the primary dressing covering the wound.

As heretofore mentioned, the concept of providing a primary dressing containing adhesiveless areas having slits therein to permit wound fluid to diffuse therethrough to an overlying reservoir, herein called a "secondary dressing" is described and claimed in copending application Ser. No. 738,983.

As stated in this copending application, the invention was predicated upon the initial discovery that an adhesive layer is essential to provide the requisite pressure build-up to open the slits. In accordance with the claimed invention, the adhesive-free areas containing the slits for removal of excess wound exudate are isolated by the adhesive coating forming a dam or barrier inhibiting lateral diffusion of the exudate so that it is instead directed upwardly through the slits provided in the dressing sheet. As further stated therein, for optimum effectiveness the ratio of surface area of the wound-covering portion which contains adhesive to the surface area in that portion which does not should be at least 1:1, i.e. at least 50% of the surface area of that portion should contain adhesive.

As is further stated in this copending application "the non-adhesive areas in theory need not be any larger than the slits to be provided therein. However, to provide optimum manufacturing tolerance for the slitting operating to be sure the slits do not at least in part inadvertently overlap into the adhesive area, it has been found that the non-adhesive areas should be a least on the order of about ⅛ inch wide in the directions of the slit. For example, if the non-adhesive areas are circular, they should have a ⅛ inch diameter; and if they are square the length and width should be on the order of ⅛ inch. In any case, one skilled in the art will understand that the minimal dimensions will depend primarily upon the preciseness of the manufacturing equipment to provide the slits accurately in the prescribed non-adhesive areas.

"In addition to permitting diffusion of wound exudate away from the wound and through the slits, it is essential that the wound dressings of this invention provide a barrier to evaporation of water (as distinguished from a barrier to removal of exudate) so as to keep the wound surface moist as excess exudate is removed.

"The benefits of maintaining a moist wound surface are of course well known and include faster reepithelialization, less pain and better cosmetic results.

"In order to do so, in accordance with the present invention the size and number of slits in the dressing should be such as to provide a dressing of the type known in the art as a moist healing wound dressing. In order to do so in accordance with this invention the size and number of slits should be such as to maintain a moisture vapor permeability or transition rate for the dressing of no greater than 1500 grams/meter/24 hours at 37° C. and 50% relative humidity.

"By way of illustration, successful results have been obtained by providing five to eight ⅛" diameter non-adhesive areas per square inch of surface area to obtain the preferred moist dressing.

"The slits will optimally extend across the width or diameter of the non-adhesive areas. With ⅛" diameter circular areas, excellent results have been obtained with cross slits across the diameter of the circle. Many other slit designs may also be employed. For example, equal success has been obtained with 3/64 inch radius half circle slits in ¼ inch diameter circles as well as S-shaped slits in ¼ inch diameter areas.

"The vented dressing of this invention may be prepared in the following manner:

(1) apply an adhesive layer of the desired thickness by calendering, casting, etc. between two release sheets of differential affinity;

(2) punch holes of the desired configuration and spacing through the thickness of the resulting "sandwich";

(3) remove the release sheet of lesser affinity from the adhesive, leaving the other release sheet of greater affinity adhering to the opposed surface of the adhesive;

(4) apply the free adhesive surface to the surface of the desired elastomeric sheet;

(5) provide slits by cutting the sheet in areas where there is no adhesive, i.e. in those areas where holes had been punched through the adhesive "sandwich"; and (6) thereafter replace the release sheet having the holes punched through it with a new one free from holes. . . ."

By way of recapitulation, the essence of the present invention is the improvement over the teachings of the aforementioned copending application Ser. No. 738,983, directed to the task of inhibiting maceration of the intact skin surrounding the wound resulting from the continued presence of the primary dressing. As heretofore stated, this task is solved by providing slit-free areas of no adhesive in the peripheral portions surrounding the wound, whereby vapor can transpire from the underlying skin while preventing escape through the sheet material of any exudate which may have diffused laterally from the edge of the wound.

As was heretofore mentioned, the concepts of employing a high density/low density absorbent material reservoir 38, 40 and a release coating 20 to facilitate separation of the two dressings are the subject matter of concurrently filed application Ser. Nos. 856,414 and 856,413, respectively.

These two concepts have been discussed earlier in this specification since they are included within the "best mode contemplated by the inventor" for carrying out the instant invention.

Accordingly, it is to be expressly understood that since these two concepts comprise no part of the invention claimed in this application, they are not essential to the practice of the invention herein claimed.

The particular selection of materials which may be employed are per se known in the art and, accordingly, their selection may be considered to be a matter of individual choice within the expected judgement of the skilled worker in the light of the foregoing description.

By way of illustration, sheet 12, which is flexible so as to be conformable to the contour of the body part to which it is to be applied, may be as thin as 0.5 mil or as thick as 5.0 mil, but is preferably on the order of 1.0 mil thick. Preferably, it is an elastomer which is characterized as being non-swellable or only slightly swellable. Most preferably, sheet 12 will be sufficiently transparent so that the underlying wound can be seen to observe the healing process. Materials useful for preparing slitted sheet 12 are well known in the art and will be readily suggested to those skilled in the art in the light of the foregoing description. By way of example, useful materials will include polyurethane, copolyesters such as "HYTREL", polyvinyl chlorides, polyolefins, etc.

The adhesive materials employed may likewise by any of the known so-called medical grade or hypoallergenic adhesives heretofore employed in securing dressings to the skin. Such known adhesives include the rubber-based, acrylic, vinyl ether and hydrocolloid pressure-sensitive adhesives. The adhesive may be applied to provide a layer of at least 1 mil thick, but preferably layers of adhesive at least 5 mils thick, e.g. on the order of 5–10 mils are contemplated.

Release coatings such as silicone for use in providing layer 20 facilitating separation of the secondary dressing are of course well known and need not be discussed in any detail.

From the foregoing description, it will thus be appreciated that the present invention is directed to a wound dressing of simplified design of the type described and claimed in the aforementioned copending application, Ser. No. 738,983 to permit removal of excess wound exudate while at the same time providing the desired moist environment promoting proper healing.

Specifically, the present invention is directed to the recited improvement thereover, wherein slit-free areas of no adhesion are provided in peripheral portions of the dressing so as to permit moisture transpiration from the underlying skin and thereby inhibit if not completely preventing maceration.

Since certain changes may be made without departing from the scope of the invention herein contemplated, it is intended that the foregoing description and accompanying drawings be taken as illustrative and not in a limiting sense.

What is claimed is:

1. A vented dressing comprising a thin, conformable vapor-permeable, liquid-impermeable sheet material having a generally centrally disposed wound-covering surface area portion for placement over a wound and a peripheral surface area portion defining the wound-covering surface area portion and which is intended to be secured in fluid-tight relationship to whole skin surrounding a wound, the sheet material having a coating of a pressure-sensitive adhesive extending substantially entirely over one surface thereof for adhering the dressing over a wound, the adhesive coating being applied so as to provide repeating surface areas in the wound-covering portion containing no adhesive, the repeating surface areas containing no adhesive being isolated by surface areas containing adhesive to form a dam or barrier inhibiting lateral diffusion of wound fluids, surface areas of the wound-covering portion of the sheet material where there is no adhesive having slits extending through its thickness to permit venting of fluid through the sheet material unimpeded by a presence of adhesive material which can clog the slits and thereby inhibit fluid transfer therethrough, each of the slits having smaller dimensions than the repeating areas of the sheet material containing no adhesive whereby each slit occupies only a portion of the area containing no adhesive in which the slit is contained, the slits being of a size and number such as to retain sufficient moisture to provide a moist healing wound dressing;

and wherein the peripheral portions also have repeating areas of no adhesive isolated by areas containing adhesive, the repeating areas of no adhesive in the peripheral portions being slit-free whereby passage of wound fluids therethrough is precluded, the repeating areas of the vapor-permeable sheet material in the peripheral portions having no adhesive permitting vapor transmission therethrough so as to inhibit maceration of underlying skin.

2. A vented dressing as defined in claim 1 characterized in that the adhesive-free areas containing the slits are isolated by the adhesive layer and the adhesive layer forms a dam or barrier inhibiting lateral diffusion of wound fluid, wherby to cause the wound fluid instead to be directed upwardly through the slits in the sheet material.

3. A vented dressing as defined in claim 2 wherein the surface area of the portion of the sheet material adapted for placement on the wound which contains adhesive with respect to the surface area of that portion which does not contain adhesive is of a ratio at least 1:1.

4. A vented dressing as defined in claim 2 wherein the non-adhesive areas containing the slits are at least about ⅛ inch wide in the direction of the slit.

5. A vented dressing as defined in claim 2 wherein the non-adhesive areas are substantially circular in configuration, the non-adhesive areas have a diameter of at least about ⅛ inch.

6. A vented dressing as defined in claim 5 wherein the non-adhesive areas have a diameter of at least about ⅛ inch.

7. A vented dressing as defined in claim 2 wherein the slits in the dressing are of a size and number to maintain a moisture vapor permeability for the dressing of no greater than about 1500 grams/meter/24 hours at 37° C. and 50% relative humidity, whereby to provide what is characterized as being a moist healing wound dressing.

8. A wound dressing comprising:
a primary dressing for placement on skin to cover a wound, the primary dressing comprising a thin, conformable, vapor-permeable, liquid-impermeable sheet material having a generally centrally disposed wound-covering portion for placement directly over the wound and a peripheral portion defining the wound-covering portion and which is intended to be secured in fluid-tight relationship to whole skin surrounding the wound, the sheet material having a coating of a pressure-sensitive adhesive extending substantially over one surface thereof for adhering the dressing over the wound, the adhesive coating being applied so as to provide repeating areas of no adhesive in the wound-covering and peripheral portions of the dressing, the repeating areas of no adhesive in the wound-covering portion of the sheet material having slits extending through its thickness to permit venting of wound fluids therethrough unimpeded by a presence of adhesive material which can clog the slits and thereby inhibit fluid transfer therethrough, each of the slits having smaller dimensions than the repeating areas of the sheet material containing no adhesive whereby each slit occupies only a portion of the area containing no adhesive in which the slit is contained, the slits being of a size and number such as to retain sufficient moisture to provide a moist healing wound dressing;
repeating areas of no adhesive in the peripheral portions being slit-free whereby passage of wound fluids therethrough is precluded, the repeating areas of the vapor-permeable sheet material in the peripheral portions permitting vapor transmission from skin whereby to inhibit maceration of skin underlying the peripheral portion of the dressing; and
a secondary dressing overlying the primary dressing containing a reservoir for receiving and retaining wound fluids diffusing thereto through the slits in the underlying primary dressing, the secondary dressing being releasably secured to the primary dressing so as to be removable for replacement by another secondary dressing on an as needed basis.

9. A wound dressing as defined in claim 8 wherein the reservoir of the secondary dressing has a capacity for receiving and retaining wound fluids and comprises an absorbent fabric, the absorbent fabric being contained between the slitted sheet material of the primary dressing and an outer cover characterized as being a bacterial barrier, at least a portion of the outer cover also being air-permeable for permitting egress of air contained in the reservoir, the egress of air therefrom appreciably increasing the capacity of the reservoir to receive wound fluids diffusing to the reservoir through the slots in the sheet material covering the wound.

10. A vented dressing as defined in claim 9 wherein the outer cover sheet and the sheet material are sealed in liquid- and bacteria-tight relationship around their common peripheral edge so that wound fluids cannot escape through the peripheral edge of the dressing, nor can any external contaminants, including bacteria enter into the dressing and then pass through the slits in the sheed material to the underlying wound.

11. A vented dressing as defined in claim 10 characterized in that the adhesive-free areas containing the slits are isolated by the adhesive layer and the adhesive layer forms a dam or barrier inhibiting lateral diffusion of wound fluid, whereby to cause the wound fluid instead to be directed upwardly through the slits in the sheet material.

12. A vented dressing as defined in claim 11 wherein the surface area of the portion of the sheet material adapted for placement on the wound which contains adhesive with respect to the surface area of that portion which does not contain adhesive, is of a ratio of at least 1:1.

13. A vented dressing as defined in claim 11 wherein the non-adhesive areas are substantially circular in configuration, the non-adhesive areas have a diameter of about ⅛ inch.

14. A vented dressing as defined in claim 11 wherein the slits in the dressing are of a size and number to maintain a moisture vapor permeability for the dressing of no greater than about 1500 grams/meter/24 hours at 37° C. and 50% relative humidity, whereby to provide what is characterized as being a moist healing wound dressing.

15. A vented dressing comprising a thin, conformable vapor-permeable, liquid-impermeable sheet material having a generally centrally disposed wound-covering surface area portion for placement over a wound and a peripheral surface area portion defining the wound-covering surface area portion and which is intended to be secured in fluid-tight relationship to whole skin surrounding a wound, the sheet material having a coating of a pressure-sensitive adhesive extending substantially entirely over one surface thereof for adhering the dressing over the wound, the adhesive coating being applied so as to provide repeating surface areas in the wound-covering portion containing no adhesive, the repeating surface areas containing no adhesive being isolated by surface areas containing adhesive to form a dam or barrier inhibiting lateral diffusion of wound fluids, the surface areas of the wound-covering portion of the sheet material where there is no adhesive having slits extending through its thickness to permit venting of fluids through the sheet material unimpeded by a presence of adhesive material which can clog the slits and thereby inhibit fluid transfer therethrough, each of the slits having smaller dimensions than the repeating areas of the sheet material containing no adhesive whereby each slit occupies only a portion of the area containing no adhesive in which the slit is contained, the slits being of a size and number such as to retain sufficient moisture to provide a moist healing wound dressing, only one of the slits being contained in each surface area of no adhesive having a slit;

and wherein the peripheral portions also have repeating areas of no adhesive isolated by areas containing adhesive, the repeating areas of no adhesive in the peripheral portions being slit-free whereby passage of wound fluids therethrough is precluded, the repeating areas of the vapor-permeable sheet material in the peripheral portions having no adhesive permitting vapor transmission therethrough so as to inhibit maceration of underlying skin.

16. A vented dressing as defined in claim 15 characterized in that the adhesive-free areas containing the slits are isolated by the adhesive layer and the adhesive layer forms a dam or barrier inhibiting lateral diffusion of wound fluid, whereby to cause the wound fluid instead to be directed upwardly through the slits in the sheet material.

17. A vented dressing as defined in claim 16 wherein the surface area of the portion of the sheet material adapted for placement on the wound which contains adhesive with respect to the surface area of that portion which does not contain adhesive is of a ratio at least 1:1.

18. A vented dressing as defined in claim 16 wherein the non-adhesive areas containing the slits are at least about ¼ inch wide.

19. A vented dressing as defined in claim 16 wherein the non-adhesive areas are substantially circular in configuration, the non-adhesive areas have a diameter of at least about ¼ inch.

20. A vented dressing as defined in claim 19 wherein the non-adhesive areas have a diameter of at least about ½ inch.

21. A vented dressing as defined in claim 16 wherein the size and number of slits in the dressing are of a size and number to maintain a moisture vapor permeability for the dressing of no greater than about 1500 grams/meter/24 hours at 37° and 50% relative humidity, whereby to provide what is characterized as being a moist healing wound dressing.

22. A wound dressing comprising:

a primary dressing for placement on a wound to cover a skin surface the primary dressing comprising a thin, conformable, vapor-permeable, liquid-impermeable sheet material having a generally centrally disposed wound-covering portion for placement directly over the wound and a peripheral portion defining the wound-covering portion and which is intended to be secured in fluid-tight relationship to whole skin surrounding the wound, the sheet material having a coating of a pressure-sensitive adhesive extending substantially over one surface thereof for adhering the dressing over the wound, the adhesive coating being applied so as to provide repeating areas of no adhesive in the wound-covering and peripheral portions of the dressing, the repeating areas of no adhesive in the wound-covering portion of the sheet material having slits extending through its thickness to permit venting of wound fluids therethrough unimpeded by the presence of adhesive material which can clog the slits and thereby inhibit fluid transfer therethrough, each of the slits having smaller dimensions than the repeating areas of the sheet material containing no adhesive whereby each slit occupies only a portion of area containing no adhesive in which the slit is contained, the slits being of a size and number such as to retain sufficient moisture to provide a moist healing wound dressing, only one of the slits being contained in each surface area of no adhesive having a slit;

repeating areas of no adhesive in the peripheral portions being slit-free whereby passage of wound fluids therethrough is precluded, the repeating areas of the vapor-permeable sheet material in the peripheral portions permitting vapor transmission from skin whereby to inhibit maceration of skin underlying the peripheral portion of the dressing; and a secondary dressing overlying the primary dressing containing a reservoir for receiving and retaining wound fluids diffusing thereto through the slits in the underlying primary dressing, the secondary dressing being releasably secured to the primary dressing so as to be removable for replacement by another secondary dressing on an as needed basis.

23. A wound dressing as defined in claim 22 wherein the reservoir of the secondary dressing has a capacity for receiving and retaining wound fluids comprises an absorbent fabric, the absorbent fabric being contained between the slitted sheet material of the primary dressing and an outer cover characterized as being a bacterial barrier, at least a portion of the outer cover also being air-permeable for permitting egress of air contained in the reservoir, the egress of air therefrom appreciably increasing the capacity of the reservoir to receive wound fluids diffusing to the reservoir through the slits in the sheet material covering the wound.

24. A vented dressing as defined in claim 23 wherein the outer cover sheet and the sheet material are sealed in liquid- and bacteria-tight relationship around their common periphery so that wound fluids cannot escape through the periphery of the dressing, nor can any external contaminants, including bacteria enter into the dressing and then pass through the slits in the sheet material to the wound.

25. A vented dressing as defined in claim 24 characterized in that the adhesive-free areas containing the slits are isolated by the adhesive layer and the adhesive layer forms a dam or barrier inhibiting lateral diffusion of wound fluid, whereby to cause the wound fluid instead to be directed upwardly through the slits in the sheet material.

26. A vented dressing as defined in claim 25 wherein the surface area of the portion of the sheet material adapted for placement on the wound which contains adhesive with respect to the surface area of that portion which does not contain adhesive, is of a ratio of at least 1:1.

27. A vented dressing as defined in claim 25 wherein the non-adhesive areas are substantially circular in configuration, the non-adhesive areas have a diameter of about ¼ inch.

28. A vented dressing as defined in claim 25 wherein the non-adhesive areas have a diameter of about ½ inch.

29. A vented dressing as defined in claim 28 wherein the non-adhesive areas have a diameter of at least of about ⅛ inch.

30. A vented dressing as defined in claim 25 wherein the size and number of slits in the dressing are of a size and number to maintain a moisture vapor permeability for the dressing of no greater than about 1500 grams/meter/24 hours at 37° C. and 50% relative humidity, whereby to provide what is characterized as being a moist healing wound dressing.

* * * * *